United States Patent [19]

Knipper et al.

[11] Patent Number: 5,514,792

[45] Date of Patent: May 7, 1996

[54] CHEMICALLY MODIFIED SUCCINOGLYCANS AND INDUSTRIAL COMPOSITIONS COMPRISED THEREOF

[75] Inventors: Magali Knipper; Michèle Raffart, both of Paris; Alain Senechal, Maison-Alfort, all of France

[73] Assignee: Rhone-Poulenc Chimie, Courbevoie Cedex, France

[21] Appl. No.: 390,420

[22] Filed: Feb. 17, 1995

Related U.S. Application Data

[63] Continuation of Ser. No. 911,734, Jul. 10, 1992, abandoned.

[30] Foreign Application Priority Data

Jul. 10, 1991 [FR] France ................................ 91 08670

[51] Int. Cl.$^6$ .............................. C12P 19/04; C12N 1/20; C07H 1/00
[52] U.S. Cl. ................ 536/124; 435/101; 435/252.2; 435/822; 536/1.11; 536/114; 536/123.12
[58] Field of Search .......................... 536/1.11, 123.12, 536/124, 114; 435/101, 252.2, 822

[56] References Cited

U.S. PATENT DOCUMENTS

| | | | |
|---|---|---|---|
| 3,754,925 | 8/1973 | Kimura et al. | 426/573 |
| 3,857,975 | 12/1974 | Misaki et al. | 426/350 |
| 4,638,059 | 1/1987 | Sutherland | 536/1.1 |
| 4,754,809 | 7/1988 | Zanten et al. | 252/8.551 |
| 4,774,093 | 9/1988 | Provonchee et al. | 536/1.1 |
| 4,873,323 | 10/1989 | Cros et al. | 536/114 |
| 4,908,310 | 3/1990 | Buller | 435/101 |
| 4,935,447 | 6/1990 | Philips et al. | 514/640 |
| 4,999,047 | 3/1991 | Schuppiser | 435/104 |
| 5,104,566 | 4/1992 | Guerin et al. | 252/174.17 |

FOREIGN PATENT DOCUMENTS

| | | |
|---|---|---|
| 0215692 | 3/1987 | European Pat. Off. . |
| 0237418 | 9/1987 | European Pat. Off. . |
| 2176795 | 1/1987 | United Kingdom . |

Primary Examiner—Herbert J. Lilling
Attorney, Agent, or Firm—Burns, Doane, Swecker & Mathis

[57] ABSTRACT

Chemically modified succinoglycan polysaccharides, e.g., acidic or enzymatic hydrolysates, have a reduced content of pyruvic acid and succinic acid structural units relative to the unmodified such succinoglycans, and are well suited, whether in fibrous, powdery or gel state, for use, e.g., as thickening stabilizing or suspending agents, in foodstuff, cosmetic and a variety of other compositions.

7 Claims, No Drawings

CHEMICALLY MODIFIED SUCCINOGLYCANS AND INDUSTRIAL COMPOSITIONS COMPRISED THEREOF This application is a continuation of application No. 07/911,734, filed Jul. 10, 1992 now abandoned.

BACKGROUND OF THE INVENTION

1. Field of the Invention

The present invention relates to novel chemically modified succinoglycans and to industrial compositions comprised thereof.

According to the present invention "succinoglycan" includes the family of polysaccharides of bacterial origin which contain, in addition to structural units derived from galactose and from glucose, structural units derived from succinic, pyruvic and, optionally, acetic acids, or from the salts of such acids.

2. Description of the Prior Art

It is known to this art that the different microorganism which are suitable for producing the above succinoglycans include, in particular, the bacteria of the Pseudomonas, Rhizobium, Alcaligenes and Agrobacterium genera.

Certain particular succinoglycans described in the literature have very desirable rheological properties under severe conditions of temperature or of pH.

Indeed, these succinoglycans exhibit rheological properties comparable to those of xanthan gum and are, furthermore, characterized by an increased stability to temperature, to acid and basic pHs and in strongly saline media.

This type of succinoglycan thus proves to be an attractive substitute for xanthan gum in industrial fields as varied as, for example, agrochemistry, the farm produce industry, the petroleum industry and cosmetics.

Various industrial applications of the succinoglycans are also known to this art. However, these applications exclusively employ succinoglycan aqueous solutions and not succinoglycan aqueous gels. A gel, however, would be very particularly desirable by reason of its greater capacities as a suspending agent and as a stabilizer, both in foodstuffs, perishable comestibles and in cosmetics.

Succinoglycan gels are described in EP-251,638, but these are essentially gels prepared via the crosslinking of succinoglycans by metal cations. These metal cations remain in the final succinoglycan gel which gels are thus unsuitable/incompatible for foodstuff applications.

SUMMARY OF THE INVENTION

Accordingly, a major object of the present invention is the provision of novel chemically modified succinoglycans and food-grade, nontoxic and stable gels/compositions formulated therefrom that are well suited for applications in the foodstuff and cosmetics industries.

Another object of the present invention is the provision of to certain processes for the preparation of such novel succinoglycans and gels/compositions comprised thereof.

Yet another object of this invention is the provision of certain improved applications of such gels/compositions.

Briefly, the present invention features compositions based on at least one polysaccharide prepared from at least one succinoglycan, such at least one polysaccharide having a reduced content of structural units derived from succinic and pyruvic acids or salts thereof relative to the number of these structural units in the starting material succinoglycan.

DETAILED DESCRIPTION OF THE PREFERRED EMBODIMENTS OF THE INVENTION

More particularly according to the present invention, the respective constituent amounts of said structural units comprising the starting polysaccharide are reduced by at least 30% in respect of the structural units derived from pyruvic acid and by at least 50% in respect of the structural units derived from succinic acid, both relative to the starting succinoglycan. In particular, the content of pyruvic acid units in the polysaccharide is preferably reduced by approximately 30% to 80% and the content of succinic acid units by approximately 50% to 80% in relation to the starting succinoglycan.

Preferably, the compositions according to the invention are based on a succinoglycan produced by the fermentation of a carbon source assimilable by a microorganism of the Agrobacterium genus.

Such microorganism is more particularly of the *Agrobacterium tumefaciens* I-736 stain, or recombinant or mutant thereof.

The compositions according to the invention can either be in the form of an aqueous gel or in the form of solids of the fibrous or powder type, which solids may be formulated into a gel in aqueous medium.

In this latter event, the gel is prepared by simple dispersion of the composition in powder form in an aqueous solvent.

The polysaccharide concentration in the gels of the invention advantageously ranges from approximately 0.1% to approximately 5%, preferably from approximately 0.2% to 1% and more preferably is about 0.2%.

The strength of such gel is, of course, variable as a function of the concentration and the nature of the starting material succinoglycan.

This gel is stable over a wide pH range and its pH can be adjusted to any desired value by simple addition of a suitable base or acid.

In the particular case of a composition derived from a succinoglycan produced by the specific strain *Agrobacterium tumefaciens* I-736, the corresponding gel is a transparent gel.

Chemical analysis of a gel produced from this specific strain evidences that for a glactose, approximately 8.6 glucose structural units and only approximately 0.26 succinic acid structural unit and approximately 0.32 pyruvic acid structural unit are present, as opposed to 0.8 succinic acid structural unit and 1 pyruvic acid structural unit present in the starting succinoglycan.

The compositions according to the invention are produced by simple acidic or enzymatic hydrolysis of at least one succinoglycan.

Thus, the present invention also features a process for preparing the subject compositions, comprising:

(a) acidifying an aqueous solution of a starting succinoglycan to a pH of at least 1.5, (b) aging or maturing, optionally with agitation, such acidified solution until it attains a minimum viscosity threshold to forms a gel and (c) recovering said gel therefrom.

Preferably, the acidification is carried out using a concentrated solution of a mineral acid.

Exemplary of such mineral acids include hydrochloric, sulfuric, nitric and phosphoric acids. Preferably, a 20% aqueous solution of sulfuric acid is used.

Organic acids can also be used, but it is difficult to attain very acidic pHs using these.

Preferably, the acid is added to approximately 0.3% aqueous solution of the succinoglycan.

Following the acidification, viscosity of the acidified solution first dramatically decreases and, in certain instances, a precipitate is formed. The gelation occurs later, during the maturation or aging step.

The kinetics of formation of the gel are linked to the strength of the acid used, to its concentration and to the storage/aging temperature of the acidified succinoglycan solutions.

Such acid solution can be stored at a temperature ranging from approximately 20° to 80° C. However, storage at a temperature higher than 40° C. and lower than 60° C. considerably accelerates the phenomenon of gelation. Preferably, the solution is aged at a temperature of about 50° C.

The gel thus obtained is stable at room temperature. Its acid pH can be readjusted, by means of a suitable basic aqueous solution, to neutrality. In respect of the strength of the gel, it is of course also variable according to the nature and the concentration of the acid.

The data appearing in the examples below reflect the influences of these different parameters—temperature, nature and acid strength—on the kinetics of formation and the strength of the gel. Thus, one skilled in this art could produce any desired gel by routine experimentation.

It too will be appreciated that such acidic gel could be used directly as an acidic descaling gel.

The addition of colorants and/or of fragrances typically present in compositions of this type, e.g., detergent compositions, is conducted prior to the gelation of the solution of acidified succinoglycan, namely, at that point in time when the viscosity attains its minimum threshold.

In a preferred embodiment of the invention, the above process additionally comprises, when the minimum viscosity threshold is reached and before the formation of the gel, a stage of precipitation of said solution using an organic liquid/solvent, the recovery of the resulting fibers and, optionally, the purification of same.

Acetone and alcohols such as ethanol, propanol, isopropanol, butanol or tertiary butanol are exemplary of such organic liquids according to the present invention. Isopropanol is more particularly preferred.

The volume of organic liquid used is generally 2 to 3 times that of the volume of polysaccharide to be treated.

The precipitation by means of the organic liquid can also be carried out in the presence of salts such as the sulfates, chlorides or phosphates of sodium, potassium or calcium.

This precipitation is preferably carried out at the storage or aging temperature of the acidic solution and by addition of this solution of acidic polysaccharide to the organic liquid. The heteropolysaccharide, once precipitated, can then be separated from the organic liquid by filtration, centrifugation or pressing. The resulting fibers thus isolation can be dehydrated, for example by means of an alcohol or of acetone. These can then be dried and crushed to produce a composition according to the invention in powder form, or else resuspended in aqueous medium to produce a composition of the invention in the form of a gel.

The starting material succinoglycan is prepared conventionally by culturing the selected strain in an appropriate fermentation medium and under appropriate temperature conditions.

More particularly, the preparation of a succinoglycan from the *Agrobacterium tumefaciens* I-736 strain is described, in detail, in Patent EP-351,303.

Briefly, the corresponding succinoglycan is produced by culturing this strain in the presence of a source of assimilable carbon of glucose, sucrose or starch hydrolysate type, of an organic nitrogen source, such as casein, caseinates, vegetable flours, yeast extracts or corn steep liquor (CSL), mineral salts such as the metal sulfates, phosphates or carbonates and, optionally, trace elements.

Of course, the different sources of carbon, nitrogen and mineral acids indicated above are exemplary only and given solely for purposes of illustration.

Typically, this fermentation is carried out at pressures from 1 to 4 bar, at a temperature ranging from 25° to 35° C. and under submerged aerobic conditions. The pH of the fermentation medium generally ranges from 5 to 9 and preferably from 6 to 8 and can be adjusted over the course of the fermentation.

The succinoglycan is then isolated from the fermentation must by successively thermally treating the must at a pH of from 6 to 8 and then precipitating the succinoglycan by means of an organic solvent and preferably of isopropanol. When separated from the must, the succinoglycan is filtered, centrifuged, pressed and dried. The fibers obtained are optionally milled before being used to prepare a composition according to the invention therefrom.

The composition of the gel type according to the invention can advantageously be used for a wide variety of industrial applications.

By virtue of its original gelified formulation, it is very particularly attractive for use as a thickening agent, suspending agent or as a stabilizing agent for dispersions.

Because it is perfectly nontoxic, it is well suited for the foodstuff industry and for cosmetic and pharmaceutical formulations. It is, of course, also well suited for more industrial applications, in the explosive industry, for example, and for the formulation of domestic or industrial cleaning and detergent compositions and of lubricating compositions.

The *Agrobacterium tumefaciens* was deposited in accordance with the Treaty of Budapest with the Collection Nationale de Culture des Microorganismes (CNCM), on 1st Mar. 1988, where it is publicly accessible under No. I-736. This strain was from the Collection Nationale de Bactéries Phytopathogènes and is listed under number CNBP 291 in the 1974 catalog.

In order to further illustrate the present invention and the advantages thereof, the following specific examples are given, it being understood that same are intended only as illustrative and in nowise limitative.

In said examples to follow, all parts and percentages are given by weight.

EXAMPLE 1

Method for the Preparation of the Starting Material Succinoglycan

| A medium containing (in g/l): | |
|---|---|
| CSL (corn steep liquor) | 11 |
| $K_2HPO_4$ | 4 |
| $MgSO_4.7H_2O$ | 0.5 |
| Sucrose | 25 |
| Portable water qs | 1 1 | was fermented by means of an *Agrobacterium tumefaciens* I-736 strain.

This medium was fermented by said strain at a temperature of 28° C. in a 20 liter Biolaffite® vessel having a working volume of 15 liters.

The medium was stirred at 400 rev/min by means of Rushton®-type stirrers.

The medium was aerated under an airflow of 825 l/h.

After 90 hours of fermentation, which corresponded to the total or virtually total consumption of the sucrose, 66% by weight of heteropolysaccharide, defined in relation to the weight of the starting sucrose, was obtained.

The viscosity of the fermentation must, measured using a Brookfield LVT® viscometer with a number 4 cylindrical spindle at 30 rev/min, was 6,800 mPa.s.

The recovery of the heteropolysaccharide was from 2 kg of this must thermally treated at 90° C. for 30 min.

To the must thus treated were added 2,300 ml of isopropyl alcohol (IPA). The precipitation was carried out in the presence of 150 g of sodium sulfate. The fibers produced by the precipitation were then dehydrated twice in the presence of 1,200 ml of IPA. The fibers were then pressed, dilacerated and dried in an oven at 85° C. The dry material obtained was milled and sieved. A cream-colored succinoglycan powder was then obtained which was used directly to prepare the gel according to the invention.

EXAMPLE 2

Method for the Preparation of a Composition According to the Invention by Acidic Hydrolysis of a Succinoglycan 2.2 g of powder produced according to Example 1 were first hydrated in 217.8 g of water. The powder was added to the water which was stirred for 20 minutes by means of a deflocculating paddle rotating at a speed of 600 rev/min. This solution was then maintained at rest for 4 hours.

220 g of a 20% hydrochloric acid solution were withdrawn and added with agitation to 220 g of the above hydrated solution. This mixture was poured into an airtight container which was stored in an oven maintained at a temperature of 50° C. This oven was equipped with a system of tumbling stirring permitting a homogeneous distribution of the temperature within the solution.

After 48 hours, the mixture was removed from the oven for the purpose of precipitating it.

900 ml of isopropyl alcohol were measured and poured into a beaker equipped with a deflocculating paddle. The beaker was placed in a water bath at 50° C. to maintain the alcohol at a temperataure of from 40° to 50° C.

The warm acidic mixture based on polysaccharide was poured dropwise into the warm alcohol with stirring at 600 rev/min. Short and swollen fibers developed within the mixture. The suspension of fibers was removed from the water bath and the stirring was continued for 20 minutes.

The suspension of the fibers was filtered on a Büchner funnel equipped with a filter paper. The fibers were reslurried with stirring in a beaker containing 400 ml of isopropyl alcohol. The fibers were dried at low temperature.

Characterization

By chemical analysis of the fibers, 8.6 glucose units, against only 0.26 of succinic and 0.32 of pyruvic units were determined for a galactose. By simple dissolution in water and at concentrations ranging from 0.1% to 1%, the product forms a translucent gel.

EXAMPLE 3

Varying the Parameters of the Preparative Process

The preparation described in Example 2 was repeated at different temperatures for various concentrations of HCl. Table I below reports the results obtained:

TABLE I

| Temperature | Acid % | Viscosities in mPa · s | | | |
|---|---|---|---|---|---|
| | | T.4h | T.7d | T.30d | T.90d |
| 20° C. | 1 | 380 | 500 | 408 | 340 |
| | 3 | 368 | 462 | 412 | |
| | 10 | 408 | 400 | 362 | 220 Gel + Late |
| 40° C. | 1 | 464 | 336 | 320 | 238 |
| | 3 | 434 | 342 | 264 | 146 |
| | 10 | 368 | 280 | 80 | Gel Gel 60D |
| 50° C. | 1 | 492 | 328 | 210 | 72 |
| | 3 | 460 | 282 | 94 | Gel 60D |
| | 10 | 358 | 224 | Gel 15D | |

EXAMPLE 4

Influence of the Nature of the Acid on the Kinetics of Formation of a Composition According to the Invention Polysaccharide gels were prepared following the procedure of Example 2 using sulfuric or phosphoric acid as the acid.

The results obtained are reported in Tables 2 and 3. They indicate that the formation of a gel is also observed with sulfuric acid and phosphoric acid.

TABLE II

| $H_2SO_4$ acid concentration (%) | Storage temperature (°C.) | Time (days) for formation of gels |
|---|---|---|
| 20 | 20–25 | 60 |
| 20 | 40 | 15–30 |
| 20 | 50 | 4 |
| 20 | 60 | 1 |
| 10 | 40 | 30 |
| 10 | 50 | 15 |

TABLE III

| Phosphoric acid concentration (%) | Storage Temperature (°C.) | Time (days) for formation of gels |
|---|---|---|
| 20 | 40 | 80 |
| 20 | 50 | 60 |
| 20 | 60 | — |

EXAMPLE 5

Determination of the Strength of the Gels

The strength of the gels, which is evaluated by the resistance of the gel to penetration, was determined using a Stevens® penetrometer at a penetration rate equal to 0.5 mm/s.

The two gels tested were prepared at an incubation temperature of 50° C., one with a 10% hydrochloric acid solution and the other with a 20% sulfuric acid solution.

In both cases, the gel tested was derived from the succinoglycan produced by the specific *Agrobacterium tumefaciens* I-736 stain.

The results obtained are reported in Table IV:

TABLE IV

| Breaking force | Concentration of polysaccharide | |
| --- | --- | --- |
| 0.96 N | HCl | 1% |
| 1.53 N | $H_2SO_4$ | 0.3% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a modified succinoglycan polysaccharide, comprising (a) acidifying an aqueous solution of an unmodified succinoglycan having pyruvic and succinic acid structural units to a pH at least as low as 1.5, (b) aging and optionally stirring said acidified solution, whereby diminishing the viscosity thereof to a minimum threshold, for a period of time to effect the gelation thereof, and (c) recovering a gel thus formed, wherein the modified succinoglycan polysaccharide of the gel has a reduced content of pyruvic and succinic acid structural units relative to the unmodified succinoglycan.

2. The process as defined by claim 1, comprising (a) acidifying with a concentrated aqueous solution of a mineral acid.

3. The process as defined by claim 2, said mineral acid comprising hydrochloric, sulfuric, nitric or phosphoric acid.

4. The process as defined by claim 3, said concentrated aqueous solution comprising an about 20% sulfuric acid solution.

5. The process as defined by claim 1, comprising (a) acidifying an about 0.3% aqueous solution of an unmodified succinoglycan.

6. The process as defined by claim 1, comprising (b) aging at a temperature ranging from about 20° to 80° C.

7. The process as defined by claim 6, comprising (b) aging at a temperature ranging from about 40° to 60° C.

* * * * *